United States Patent [19]

Gainutdinova et al.

[11] Patent Number: 4,807,610

[45] Date of Patent: Feb. 28, 1989

[54] INTRAUTERINE CONTRACEPTIVE DEVICE

[75] Inventors: Raisa V. Gainutdinova; Boris A. Jurov; Bentsian M. Mazo; Vera M. Petrova, all of Kazan, U.S.S.R.

[73] Assignee: Nauchno-Proizvodstvennoe Objedinenie "Medinstrument", Kazan, U.S.S.R.

[21] Appl. No.: 94,417

[22] Filed: Sep. 9, 1987

[51] Int. Cl.$^4$ .............................................. A61F 5/46
[52] U.S. Cl. ........................ 128/830; 128/832; 128/833; 128/839
[58] Field of Search ........................................ 128/130

[56] References Cited

U.S. PATENT DOCUMENTS

| 3,834,378 | 9/1974 | Lerner et al. | 128/130 |
| 4,111,196 | 9/1978 | Emmett | 128/130 |
| 4,562,835 | 1/1986 | Anderson | 128/130 |
| 4,572,162 | 2/1986 | Livesay et al. | 128/130 |
| 4,578,076 | 3/1986 | Luukkainen et al. | 128/130 |
| 4,582,052 | 4/1986 | Dunn et al. | 128/130 |
| 4,678,463 | 7/1987 | Millar | 128/130 |

Primary Examiner—Robert A. Hafer
Assistant Examiner—Charles H. Sam
Attorney, Agent, or Firm—Fleit, Jacobson, Cohn & Price

[57] ABSTRACT

An intrauterine device comprises a strip, a rod interconnected with the strip to form a T-shaped element therewith, a coil mounted on the rod, and a thread connected to the rod for dynamic monitoring of the IUD while in the uterine cavity. The coil has at least two layers, of which the first layer is made of an elastic polymer material, serves as a base, and faces directly the rod, while the second layer is made of metal.

4 Claims, 1 Drawing Sheet

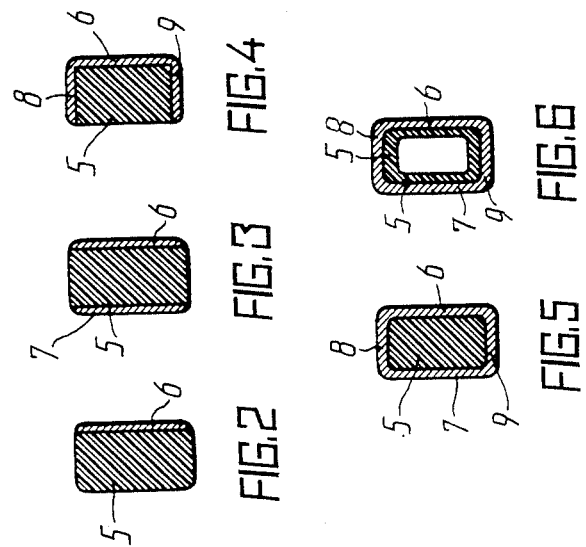
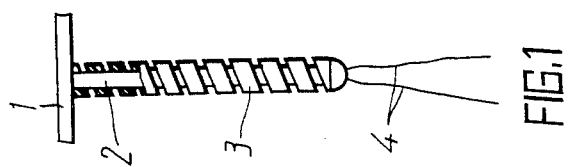

4,807,610

INTRAUTERINE CONTRACEPTIVE DEVICE

TECHNICAL FIELD

The present invention relates generally to contraceptives and more specifically to intrauterine devices (IUD).

The invention is applicable in gynecological practice for prevention of an undesirable pregnancy, as well as a preventive measure aimed at birth control and family planning.

BACKGROUND ART

Known in the art is an intrauterine device (U.S. Pat. No. 4,198,966), comprising a strip, a rod carrying a copper coil and interconnected with the rod to form a T-shaped element therewith, and a dynamic monitoring thread attached to the rod.

The coil of the known device is made of a copper wire featuring high degree of purity, i.e., from chemically pure copper, which adds to the weight of the entire device and to the danger of expulsion. The copper coil is liable to gradually dissolve in the course of a prolonged exploitation and finally to break, thus forming sharp sticking out ends which inflicts injury upon the uterine walls and causes bleeding.

Also known in the art is an intrauterine device produced by (Huhtamäki Co., Leiras, Finland, comprising a strip, a rod connected to the strip to form a T-shaped element, a coil from silver-based copper wire mounted on the rod, and a thread for dynamic monitoring of the IUD while in the uterine cavity, fixed at the rod end.

The foresaid known device is characterized by the fact that the coil made from silver-based copper wire adds to the weight of the entire device, thus enhancing the danger of expulsion.

SUMMARY OF THE INVENTION

It is therefore an objective of the invention to reduce expulsion of the device.

It is another objective of the invention to rule out any traumatic lesion of the uterine cavity.

These objects may be accomplished by an intrauterine device, comprising a strip, a rod connected to the strip to form a T-shaped element therewith, a coil mounted on the rod, and a thread connected to the rod for dynamic monitoring of the intrauterine device while in the uterine cavity. The coil is composed of at least two layers, the first layer being made of an elastic polymer material serving as a base and facing the rod, while the second layer is made of metal.

In another embodiment the coil of the intrauterine device of the invention has a third layer made of metal located on the first layer adjacent to the rod.

In another embodiment of the intrauterine device of the invention the coil has two lateral layers each made of metal and located on the first layer.

In another embodiment of the intrauterine device of the invention the polymeric layer of the coil is hollow for performing complex contraception.

Thus, provision of the coil base made from an elastic polymer material in all the embodiments mentioned above render the entire device light in weight and ensures against breaking of the coil upon complete dissolution of its metallic layers, thereby making the coil fully atraumatic.

BRIEF DESCRIPTION OF THE DRAWINGS

FIG. 1, is a side view of the intrauterine device.

FIG. 2 shows a portion of the coil 3 FIG. 1 on a larger scale and taken in cross section along a plant parallel to the long axis of rod 2 and perpendicular to the coil 3 of FIG. 2.

FIGS. 3–4 show other embodiments of coil 3 of FIG. 1.

BEST MODE FOR CARRYING OUT THE INVENTION

The intrauterine device (FIG. 1) comprises a strip 1, a rod 2 interconnected with the strip 1 to form a T-shaped element therewith, a coil 3 mounted on the rod 2, and a thread 4 connected to the rod for dynamic monitoring of the IUD while in the uterine cavity.

Given below are some specific embodiments of the herein-disclosed intrauterine device featuring the various constructional arrangements of the coil.

The coil 3 is constituted by two layers (FIG. 2), a first layer 5 being made of an elastic polymer material, serves as the base and faces directly the rod 2 (FIG. 1), while a second layer 6 (FIG. 2) is made in metal. In addition, the coil 3 (FIG. 1) has a third layer 7 (FIG. 3) made also in metal and located on the first layer 5 so as to face the rod 2 (FIG. 1). The coil 3 has two lateral layers 8, 9 (FIGS. 4, 5) each made in metal and located on the first layer 5. The first layer 5 which serves as a base, is made hollow for use of complex contraception. In all the embodiments mentioned above the metallic layers applied to the base are made of, e.g., copper, silver, or nickel.

The intrauterine device of the invention operates as follows.

The IUD that has preliminarily been arranged in a straight line by bringing the strip 1 in alignment with the rod 2, together with the coil 3 and the dynamic monitoring thread 4, is fitted into a special syringe (not shown in the drawings). Then the IUD is inserted, with the aid of the syringe, directly into the uterine cavity, wherein the device assumes the position that suits the shape of the uterine cavity. When in the uterine cavity the device is pressed by the strip 1 against the uterine wall, while the free ends of the dynamic monitoring thread 4 emerge from the uterine cervix.

The metallic layers of the coil 3 are liable to gradually dissolve in the course of the IUD operation, but upon their complete dissolution the coil base made of an elastic polymer material does not break, which rules out perforation of the uterine walls causative of bleeding, and reduces the danger of traumatic lesion. In addition, use of a coil provided with an elastic base and metallic layers applied thereto as described above, in the described above IUD reduces the weight of the entire device and hence renders the danger of expulsion and traumatism less possible.

Industrial Applicability

The invention can find application in gynecological practice for prevention of an undesirable pregnancy, as well as a preventive measure aimed birth control and family planning.

What is claimed is:

1. An intrauterine device, comprising:
   a strip;
   a rod interconnected with said strip to form a T-shaped element therewith;

a thread for dynamic monitoring of the intrauterine device while in the uterine cavity, said thread being connected to said rod;

a coil fitted over said rod and having a base made of an elastic polymer material, said base facing directly to said rod, and a metallic layer coated on said base.

2. An intrauterine device a claimed in claim 1, comprising:

a second metallic layer located on said base of said coil, interposed between said rod and said base.

3. An intrauterine device as claimed in claim 1, comprising:

a pair of metallic lateral layers located on said base.

4. An intrauterine device as claimed in claim 3, wherein said base is hollow for application of complex contraception.

* * * * *